United States Patent
Nufer et al.

(10) Patent No.: US 12,348,905 B2
(45) Date of Patent: Jul. 1, 2025

(54) APPARATUS AND METHOD TO SUPPORT MONITORING OF A PATIENT

(71) Applicant: Siemens Healthineers AG, Forchheim (DE)

(72) Inventors: Stephan Nufer, Erlangen (DE); Felix Horn, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 134 days.

(21) Appl. No.: 17/942,509

(22) Filed: Sep. 12, 2022

(65) Prior Publication Data
US 2023/0083173 A1   Mar. 16, 2023

(30) Foreign Application Priority Data
Sep. 13, 2021   (EP) ..................................... 21196309

(51) Int. Cl.
*H04N 7/18*   (2006.01)
*A61B 5/00*   (2006.01)
*G02B 27/01*   (2006.01)

(52) U.S. Cl.
CPC ............. *H04N 7/181* (2013.01); *A61B 5/742* (2013.01); *G02B 27/0101* (2013.01); *G02B 2027/0138* (2013.01); *G02B 2027/014* (2013.01); *G02B 2027/0141* (2013.01)

(58) Field of Classification Search
CPC .... H04N 7/181; A61B 5/742; G02B 27/0101; G02B 2027/0138; G02B 2027/014; G16H 30/20; G16H 40/63; G16H 40/67; G16H 30/40
See application file for complete search history.

(56) References Cited

U.S. PATENT DOCUMENTS

| | | | | |
|---|---|---|---|---|
| 2010/0070299 A1* | 3/2010 | Datema | .................. | G16H 20/17 705/2 |
| 2012/0293606 A1* | 11/2012 | Watson | .................. | H04N 23/60 348/E7.085 |
| 2013/0127620 A1* | 5/2013 | Siebers | ................. | A61B 5/1113 340/573.1 |

(Continued)

FOREIGN PATENT DOCUMENTS

EP   2813959 A2   12/2014

OTHER PUBLICATIONS

"Windows and Shop Windows Projection Films—ADWindow front & rear projection films" Internet page (https://www.adwindowscreens.com/windows-and-shop-windows-projection-films/) dated 2015-2017 visited on Mar. 13, 2024 (Year: 2015).*

*Primary Examiner* — Sath V Perungavoor
*Assistant Examiner* — Paramita Ghosh
(74) *Attorney, Agent, or Firm* — Banner & Witcoff Ltd.

(57) ABSTRACT

A monitoring system for monitoring a patient in an examination space of an imaging apparatus may include an interface, a computing device and an output device. The interface can receive process data of the imaging examination and transfer it to the computing device. The computing device may process the process data and control the output device to provide an item of information of the imaging examination based on the process data. The monitoring system enables visual monitoring of the patient and of the item of information using the output device.

20 Claims, 5 Drawing Sheets

(56) References Cited

U.S. PATENT DOCUMENTS

| | | | | |
|---|---|---|---|---|
| 2014/0368545 A1* | 12/2014 | Ban | .................... | G01R 33/546 |
| | | | | 345/634 |
| 2015/0073816 A1* | 3/2015 | Ha | ...................... | G16H 50/70 |
| | | | | 705/2 |
| 2016/0267759 A1* | 9/2016 | Kerzner | ................ | H04N 7/181 |
| 2020/0348426 A1* | 11/2020 | Kimura | ................ | G01T 1/2978 |
| 2023/0260139 A1* | 8/2023 | Nagata | .................. | G06T 7/292 |
| | | | | 382/103 |

* cited by examiner

FIG 5

APPARATUS AND METHOD TO SUPPORT MONITORING OF A PATIENT

CROSS REFERENCE TO RELATED APPLICATIONS

This patent application claims priority to European Patent Application No. 21196309.5, filed Sep. 13, 2021, which is incorporated herein by reference in its entirety.

BACKGROUND

Field

The disclosure relates to a monitoring system for monitoring a patient in an examination space of an imaging apparatus. The disclosure also relates to a method for providing an item of information in respect of an imaging examination of a patient with a monitoring system.

Related Art

During an imaging examination of a patient it is typically necessary that a user of an imaging apparatus, such as a member of medical staff, can visually monitor the patient for the entire duration of the imaging examination. Monitoring of this kind can be necessary for example to establish whether a patient needs help or a predetermined respiratory movement is being performed correctly. The surroundings of the imaging apparatus, such as a strong magnetic field or ionizing radiation, make it necessary that the user controls the imaging apparatus from a separate control room, while the patient to be examined remains in an examination space inside the imaging apparatus. This results in a physical distance or separation between the user and the patient, which makes interaction of the user with the patient difficult and can hinder preparation and/or implementation of the imaging examination.

The patient is conventionally monitored by the user by means of a special monitoring window, which, depending on the imaging apparatus used, has to satisfy different requirements with regard to the interaction with (electromagnetic) radiation. This includes an optimally high impermeability to ionizing radiation, but also radiation in the radio-frequency range, as is used in magnetic resonance apparatuses. Such monitoring windows are conventionally associated with significant costs. Furthermore, owing to structural conditions or a sequence of the imaging examination, it is not always guaranteed that the user can adequately monitor the proceedings in the examination space.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to improve monitoring of a patient during an imaging examination.

The inventive monitoring system, according to exemplary embodiments, for monitoring a patient in an examination space of an imaging apparatus may include an interface, a computing unit, and an output unit.

An imaging apparatus can represent any medical device, which may be configured to capture image data of a body region of a patient. In an exemplary embodiment, an imaging apparatus may be configured to acquire two-dimensional and/or three-dimensional image data, in particular time-dependent three-dimensional image data, of the body region of the patient. Examples of imaging apparatuses are magnetic resonance apparatuses, X-ray apparatuses, computed tomography units, single photon emission computed tomography units, positron emission tomography units, but also mammography apparatuses and the like. In an exemplary embodiment the imaging apparatus is configured as a magnetic resonance apparatus.

The monitoring system has components, such as the interface, the computing unit and the output unit. Furthermore, the monitoring system can have further components, such as a sensor, a memory unit, a controller, signal links between the components and the like. The components of the monitoring system can be electrically and/or mechanically connected together. It is conceivable that the components form a structural unit or are positioned at different locations in an examination space and/or a control room. Furthermore, the components can be positionable relative to each other. For example, the output unit and the computing unit can be positioned in the control room, while the interface is positioned in the examination space. In a further example the interface, the computing unit and the output unit are positioned in the control room, with the interface being connected by means of a signal link to a sensor and/or the imaging apparatus in the examination space. A signal link between components in the control room and components in the examination space may be implemented by means of a fiber-optic cable or an optical connection. It is likewise conceivable, however, that the signal link is implemented by means of any electric and/or a wireless connection.

The interface may be configured to receive process data in respect of the imaging examination and to transfer it to the computing unit. It is conceivable that the interface is configured as a communications interface. The interface can also be designed as a data interface and/or as a sensor. The sensor may be configured to capture process data in respect of the imaging examination.

Process data can represent any data, which is associated with the imaging examination. For example, the process data can comprise physiological data of the patient, patient information, parameters of the imaging examination, optical image data of the patient or the like. The process data can be received by means of the interface from a sensor, the imaging apparatus and/or any imaging-relevant component.

The computing unit may be configured to process the process data and to actuate the output unit to provide information in respect of the imaging examination as a function of the process data. The output unit can comprise any output device, such as a screen, a transparent screen, a projector, a touchscreen, a loudspeaker, but also a plurality of such output devices. The computing unit may include a CPU (central processing unit) and/or a GPU (graphics processing unit), which enables processing of process data, in particular also optical data and/or image data. Processing the process data can comprise in particular extracting items of information, correlating items of information, compressing data, transforming or converting data, classifying data and/or selecting data.

A user of the imaging apparatus can represent in particular a member of medical staff, such as a nurse, a doctor, a medical-technical radiology assistant (MTRA) or the like.

An imaging examination can represent an imaging examination of a patient for acquiring images of a diagnostically relevant body region of the patient. An imaging examination can in particular represent a procedure in which radio-frequency electromagnetic waves are emitted into an image acquisition region of the imaging apparatus and radio-frequency signals from the image acquisition region are detected with a frequency and power range of conventional magnetic resonance signals.

The imaging examination may include all processes and/or phases necessary for capturing diagnostic image data of the body region of the patient, in particular planning, preparation and implementation of the imaging examination. The imaging examination can comprise one or more parameter(s), in particular imaging parameters, and/or one or more imaging sequence(s). An imaging parameter can represent a boundary condition or a variable or an imaging sequence with which capturing diagnostic image data of the body region of the patient may be established.

The imaging examination can also comprise one or more process(es). A process can represent any segment of the imaging examination. For example, a process can comprise a positioning of a patient couch, a positioning of a patient, a positioning of a body region of the patient, a positioning of a local coil, starting an imaging sequence, registering the patient, informing the patient, an anesthesia, a surgical intervention, a minimally invasive intervention or the like.

An item of information in respect of the imaging examination can relate to any item of information, which is relevant to monitoring of the patient and/or coordination of the imaging examination. The information in respect of the imaging examination can comprise any items of information ascertained as a function of the process data. In an exemplary embodiment, the information in respect of the imaging examination comprises information about a physiological state and/or a mental state of the patient.

The information in respect of the imaging examination can be obtained by means of a correlation of process data. It is also conceivable that the information in respect of the imaging examination comprises images or moving images, which are created on the basis of the process data. The images or moving images can relate in particular to the patient in the examination space. In one example the computing unit may be configured to convert optical image data captured by means of an optical sensor, such as a CCD sensor and/or a CMOS, into images or moving images and to provide them by means of the output unit. In a further example the computing unit may be configured to extract the information in respect of the imaging examination using image data of the optical sensor. Such an item of information in respect of the imaging examination can be for example a respiratory curve, which is ascertained as a function of a video recording of the patient.

The item of information in respect of the imaging examination can also define and/or trigger an action of the user dependent on a procedure of the imaging examination. Examples of this are a positioning of the patient and/or an imaging-relevant component for the imaging examination, a termination and/or a repetition of a segment of the imaging examination, but also a representation of outstanding and/or concluded steps of the imaging examination.

The monitoring system may be configured to enable visual monitoring of the patient and the information in respect of the imaging examination by means of the output unit. In an exemplary embodiment, the output unit may be configured to overlay the information in respect of the imaging examination on a field of vision of the patient and/or a digital map of the patient. This can mean that the information in respect of the imaging examination is positioned in the field of vision of the user, while the user visually monitors the patient. Concealment of an outline or a contour of the patient by the information in respect of the imaging examination can be avoided in the process. The monitoring system is in particular configured to output the visual monitoring of the patient and the information in respect of the imaging examination simultaneously to the user of the imaging apparatus.

By means of the inventive monitoring system, items of information in respect of the imaging examination may be integrated in the user's field of vision of the patient or be overlaid on it. Distraction of the user, for example owing to retrieval of patient information and/or monitoring of parameters of the imaging examination by means of a separate system, can advantageously be reduced or avoided as a result. The efficiency and/or quality of the monitoring of the patient may advantageously be increased, therefore.

In one embodiment of the inventive monitoring system, the output unit comprises a projector, wherein the projector may be configured to project the information in respect of the imaging examination onto a monitoring window of the examination space. The projector can be positioned in the examination space or the control room. In an exemplary embodiment, the projector may be configured to project the information in respect of the imaging examination onto the monitoring window in the form of images or graphical representations.

The monitoring window may be configured to make it possible for a user of the imaging apparatus to view the patient in the examination space, wherein the computing unit may be configured to actuate the output unit to overlay the information in respect of the imaging examination on the field of vision of the user through the monitoring window by means of the projector. The computing unit may be configured to provide the information in respect of the imaging examination in such a way that the information in respect of the imaging apparatus is overlaid on a display or an image of the patient and/or the user's field of vision of the patient.

The monitoring window can be part of the monitoring system or be present separately from the monitoring system. In an exemplary embodiment, the monitoring window is transparent in order to enable a view of the patient in the examination space from the control room. On a side facing the projector the monitoring window can have a layer or a coating, which may be configured to break an optical signal of the projector in such a way that visibility of the information in respect of the imaging examination is enabled or improved for the user.

A projector represents a particularly inexpensive and/or easy-to-implement possibility for overlaying the information in respect of the imaging examination on the field of vision of the user without compromising the visual monitoring of the patient by the user.

In a further embodiment of the inventive monitoring system, the output unit has a transparent screen, which may be configured to enable a user of the imaging apparatus to view the examination space through the transparent screen. With a transparent screen an active matrix or a field of view of the screen can be configured to be transparent, so a user can look through the screen. The active matrix or the field of view can be characterized by an arrangement of individual image elements (pixels) with electronic units, such as a diode, a transistor, a capacitor or the like. The individual image elements can be embedded in a transparent substrate or be held by one. The technology of the transparent screen may be based on LCD, LED or OLED technology.

The computing unit may be configured to actuate the output unit to overlay the information in respect of the imaging examination by means of the transparent screen on the field of vision of the user through the transparent screen. The computing unit can also be configured to provide the information in respect of the imaging examination in such a way that the information in respect of the imaging apparatus is overlaid on a display of the patient and/or the user's field of vision of the patient through the transparent screen. In an exemplary embodiment, the computing unit is also configured to provide items of information in respect of the imaging examination, which relate to the patient and/or an imaging-relevant component, in such a way that the items of information in respect of the imaging examination are arranged on the patient and/or the imaging-relevant component in the field of vision of the user.

By providing the transparent screen, any items of information in respect of the imaging examination may advantageously be arranged in the field of vision of the user, so the monitoring of the patient in the examination space can be improved. Furthermore, images of the patient acquired by means of a camera can also be arranged on the transparent screen, so visual monitoring possibilities for the user are advantageously expanded. Furthermore, when a projector and/or a transparent screen is used, visual monitoring of the patient can also still be enabled if it is not possible to provide the information in respect of the imaging examination owing to failure of a component of the monitoring system.

In accordance with a further embodiment, the inventive monitoring system has a camera, which is positioned in the examination space. The camera may be configured to capture optical image data of the patient in the examination space and to transfer it to the interface, wherein the computing unit may be configured to create images of the patient as a function of the optical image data and to provide them by means of the output unit.

The camera can be configured for example as a 2D camera, a 3D camera and/or an infrared camera. In an exemplary embodiment, the monitoring system has a plurality of cameras, which capture optical image data of the patient from different directions. In one embodiment the monitoring system has a first camera, which may be configured to capture optical image data of a portion of the patient, which is positioned on a patient positioning apparatus of the imaging apparatus outside of an imaging region of the imaging apparatus. The monitoring system can also have a second camera, which may be configured to capture optical image data of a portion of the patient, which is positioned inside the imaging region. In one embodiment the computing unit of the monitoring system may be configured to ascertain a position of the patient in the examination space, in particular a position of the patient relative to the imaging apparatus. The computing unit can adjust the information more in respect of the imaging examination as a function of the ascertained position of the patient. For example, the computing unit can be configured to select optical image data of one or more camera(s) as a function of the position of the patient relative to the imaging apparatus and to automatically provide it to the user as an image and/or a video by means of the output unit. The computing unit can likewise be configured to ascertain and/or evaluate a facial expression of the patient captured by the first camera and/or the second camera in order to determine the information about the physiological state and/or the mental state of the patient.

The monitoring system can also have at least one sensor, which may be configured to ascertain the position of the patient relative to the imaging apparatus and/or a position of an imaging-relevant component. A sensor of this kind can be for example a distance sensor and/or a position generator on an imaging-relevant component, such as the patient positioning apparatus. Similarly, a camera can be taken to mean a sensor of this kind. In this case, the computing unit may include an image processing unit, which may be configured to ascertain the position of the patient relative to the imaging apparatus, but also a position of the patient in the examination space. Apart from the examination space, a camera can also be positioned in a patient waiting area in order to capture optical image data of patients in the patient waiting area.

By providing a camera or a plurality of cameras the user's view of the patient may be improved compared to a monitoring window, which is conventionally positioned at a greater distance from the imaging apparatus and has a predetermined field of vision. By providing a plurality of cameras, optical image data of the patient may advantageously be captured from different directions, whereby monitoring of the patient can be improved further. Furthermore, by automatic selection of a camera, which at a given instant enables a good or optimum view of the patient, particularly advantageous monitoring of the patient by the user can be enabled. A further advantage consists in that the captured optical image data of the patient can be provided by means of the output unit in any size by means of the output unit. Members of medical staff, who are positioned in the control room and/or the examination space at a greater distance from the output unit of the monitoring system, can also perceive items of information in respect of the imaging examination and/or images of the patient.

In a further embodiment of the inventive monitoring system, the output unit comprises a screen. A screen can be any screen, which may be configured to display images of the patient. The output unit can in particular be configured to enable an image refresh rate of more than 20 images per second in order to provide moving images, for example a video signal with image data of the patient. An active matrix or a field of view of the screen may be opaque in this embodiment.

The computing unit may be configured to provide images of the patient in the examination space by means of the screen. The computing unit can be designed in particular to overlay images of the patient with further information in respect of the imaging examination. The images of the patient may be based on optical image data of the patient, which is captured by means of a sensor, such as a camera or a plurality of cameras. It is conceivable that the computing unit may be configured to select the optical image data of the patient to be provided and to overlay it with further information in respect of the imaging examination on the field of view of the screen. The computing unit can also be configured to provide optical image data of a plurality of cameras synchronously by means of the screen.

By using a screen for monitoring the patient, costs for the monitoring system may advantageously be reduced compared to a conventional monitoring window. Furthermore, an automatic selection of optical image data of a plurality of cameras can always ensure a good or optimized user's view of the patient.

In a further embodiment, the inventive monitoring system has at least one sensor, which is positioned in the examination space of the imaging apparatus and may be configured to capture process data from the examination space. The at least one sensor can be configured to capture any measurement data from the examination space. For example, the at least one sensor can be configured as a temperature sensor, a humidity sensor, a sound sensor, an optical sensor, a sensor of a medical device or the like. The at least one sensor can in particular be designed as a camera in accordance with an embodiment described above. It is also conceivable that the at least one sensor is configured as a position generator and/or a distance meter. A sensor of this kind can be designed in particular to acquire a position of an imaging-relevant component, in particular of a patient positioning apparatus or a patient couch. The computing unit can accordingly be configured to select a camera and/or a signal of a camera and provide it to the user by means of the output unit.

The interface may be configured to receive the process data from the at least one sensor and to transfer it to the computing unit, wherein the information in respect of the imaging examination is based on the process data of the at least one sensor. The information in respect of the imaging examination can comprise images and/or moving images, which are created by means of the computing unit from captured optical image data of a camera. It is likewise conceivable that the information in respect of the imaging examination comprises a marking of the patient, in particular a body region of the patient, which by means of the computing unit is overlaid on the field of vision of the user during visual monitoring of the patient. Furthermore, the information in respect of the imaging examination can comprise a graphical representation of the process data and/or a result of a correlation of a plurality of items of process data, which is overlaid on the field of vision of the user during monitoring of the patient.

By providing at least one sensor, which may be configured to capture process data from the examination space, a plurality of items of measurement data relevant to the imaging examination can advantageously be positioned in the field of vision of the user. Furthermore, as a function of process data of the at least one sensor or the plurality of sensors, items of information may advantageously be generated, which would otherwise be inaccessible to the user or could only be reproduced using a further technical facility. Consistent and/or uninterrupted monitoring of the patient can thus be enabled.

In a further embodiment of the inventive monitoring system, the at least one sensor may be configured to capture at least one of the following items of process data:
  a medical parameter of the patient,
  a parameter of an imaging-relevant component,
  a measured value of a medical device.

A medical parameter of the patient can relate in particular to vital data and/or physiological measurement data of the patient. Examples of this are respiratory behavior, an electrocardiogram, blood oxygen saturation, a temperature or the like. A parameter of an imaging-relevant component can comprise, for example, position data of a patient couch or a patient positioning apparatus. A measured value of a medical device can comprise, for example, image data of a further imaging examination, such as an ultrasound measurement, a positron emission tomography measurement, a single photon computed tomography measurement, but also an elasticity measurement or the like. The information in respect of the imaging examination, ascertained as a function of the process data, can relate to a condition of the patient during the imaging examination. It is in particular conceivable that the information in respect of the imaging examination comprises a warning indication or an alarm, which indicates a critical condition of a patient. An indication of this kind can relate to a procedure of the imaging examination, however, in which particular awareness of the user is demanded. Furthermore, the indication can also relate to a condition of the imaging apparatus, in particular a device status of the imaging apparatus.

Visual monitoring of the patient may be expanded by relevant data in respect of the condition of the patient using physiological measurement data of the patient. Monitoring of the patient during the imaging examination, in particular an identification of an adverse reaction of the patient to the imaging examination, can advantageously be improved as a result. By providing further, above-mentioned process data, the user can advantageously be given a consolidated overview of a status of the patient during the imaging examination.

In accordance with one embodiment of the inventive monitoring system, the interface has a signal link to the imaging apparatus. The interface may be configured to receive process data from the imaging apparatus and to transfer it to the computing unit, wherein the process data relates to a parameter of the imaging examination and/or an item of patient information.

A parameter of the imaging examination can be any parameter, which is characteristic of and/or decisive for the imaging examination and/or a procedure of the imaging examination. A parameter of the imaging examination can in particular represent an imaging sequence, a succession of imaging sequences and/or an imaging parameter of an imaging sequence. An imaging parameter can comprise a boundary condition or a variable of an imaging sequence with which capturing of image data of a body region of the patient may be established. Examples of imaging parameters are an image resolution, a contrast, a signal-to-noise ratio, a specific absorption rate, an echo time, a repetition time or the like. It is likewise conceivable that the parameter of the imaging apparatus comprises a group of imaging parameters and/or a succession of imaging sequences. Furthermore, a parameter can comprise any setting of the imaging examination and/or a progression of the imaging examination.

The imaging examination can also comprise one or more process(es). A process can represent any segment of the imaging examination. For example, a process can comprise a positioning of a patient couch, a positioning of a patient, a positioning of a body region of the patient, a positioning of a local coil, starting of an imaging sequence, registering the patient, informing the patient, an anesthesia, a surgical intervention, a minimally invasive intervention or the like.

In an exemplary embodiment the information in respect of the imaging examination comprises a progression and/or a status, a remaining duration, a current imaging sequence and/or an item of information about a parameter or a parameter set of the imaging examination. The computing unit is accordingly configured to overlay the information in respect of the imaging examination on the field of vision of the user by means of the output unit during visual monitoring of the patient.

An item of patient information can comprise any patient-related data. For example, the patient information comprises registration data of the patient, but also items of information about medical history, age, weight, sex and/or demographic data of the patient.

In an exemplary embodiment, the interface has a signal link to a computing unit and/or a controller of the imaging apparatus in order to receive the process data from the imaging apparatus. The signal link can be wireless or wired in accordance with an embodiment described above.

Advantageously, the user can be made aware of a state and/or a pre-existing condition of the patient, which can make implementation of the examination difficult, by providing an item of patient information in the user's field of vision of the patient. By providing the information in respect of the imaging examination on the basis of a parameter of the imaging examination, the user can advantageously be made aware of a progression and/or a progression of the imaging examination, without interrupting the visual monitoring of the patient.

In an exemplary embodiment of the inventive monitoring system the computing unit may be configured to provide a plurality of items of information in respect of the imaging examination by means of the output unit. The plurality of the items of information in respect of the imaging examination can be based in particular on a plurality of items of process data in accordance with the above-described embodiments.

The computing unit is also configured to adjust a type, an arrangement and/or an instant of the provided items of information in respect of the imaging examination as a function of the process data. The computing unit can in particular be configured to arrange the items of information in respect of the imaging examination by means of the output unit in such a way that a direct view of the patient is unrestrictedly possible. For example, the computing unit can be configured to arrange the items of information in respect of the imaging examination by means of the output unit in such a way in the field of vision of the user that an outline or a contour of the patient remains unconcealed by the provided items of information in respect of the imaging examination. It is also conceivable that items of information in respect of the imaging examination are arranged with reference to vital data of the patient in the field of vision of the user in the immediate vicinity of the patient. Such items of information in respect of the imaging examination can partially or completely overlay the outline or the contour of the patient in the field of vision of the user or prevent concealment of the patient.

In an exemplary embodiment, the computing unit may be configured to adjust the type, arrangement and/or the instant of the provided items of information as a function of a position of the user in the control room and/or a direction of the user's view of the patient. It is also conceivable that selected items of information in respect of the imaging examination, such as a remaining duration of the imaging examination or a change in imaging sequence, are output to the user at predetermined instants. A predetermined period can be for example a pending end of the imaging examination and/or a change in an imaging sequence. Furthermore, the computing unit can be configured to highlight items of information in respect of the imaging examination with current relevance to the monitoring of the patient and/or the implementation of the imaging examination. Highlighting can comprise for example a selection, but also an adjustment of a color and/or a variable of the information in respect of the imaging examination and a marking of corresponding items of information in respect of the imaging examination.

The user's view of the patient can advantageously be improved or optimized by adjusting the type, arrangement and/or of the instant of the provided items of information in respect of the imaging examination. Furthermore, the items of information in respect of the imaging examination may advantageously be provided to the user as a function of their relevance, whereby overloading or distraction of the user due to a large number of items of information in respect of the imaging examination can be avoided.

The inventive method for providing an item information in respect of an imaging examination of a patient, with a monitoring system with an interface, a computing unit and an output unit has the following steps:

receiving process data by means of the interface,
processing the process data by means of the computing unit and
providing the information in respect of the imaging examination as a function of the process data by means of the output unit.

The monitoring system can be configured in accordance with an embodiment described above. The inventive method shares the advantages of the inventive monitoring system.

In one embodiment of the inventive method, receiving process data comprises receiving optical image data of a plurality of cameras. In an exemplary embodiment, the plurality of cameras captures optical image data of the patient from different directions. The plurality of cameras can comprise a first camera and a second camera. The first camera can capture optical image data of the patient on the patient positioning apparatus from a bird's eye view, while the second camera captures optical image data of the patient in the image acquisition region of the imaging apparatus.

Processing the process data comprises ascertaining a position of the patient relative to the imaging apparatus and ascertaining a primary camera of the plurality of cameras as a function of the position of the patient relative to the imaging apparatus. The process data may be processed by means of an image processing unit of the computing unit as a function of the captured optical image data. It is likewise conceivable, however, that processing the process data comprises processing process data of at least one further sensor, such as a distance sensor and/or a position generator. In an exemplary embodiment, the distance sensor and/or the position generator detect a position of the patient positioning apparatus and/or of the patient couch, by means of which the patient is positioned in the image acquisition region of the imaging apparatus. The primary camera can be ascertained in particular as a function of the ascertained position of the patient relative to the imaging apparatus. In an exemplary embodiment, the primary camera represents a camera in the examination space, which enables a good or optimum view of the patient at a current instant.

Providing the information in respect of the imaging examination comprises outputting images of the primary camera by means of the output unit. Outputting images can in particular also comprise outputting moving images, such as of a video.

By ascertaining the primary camera, a camera may advantageously be automatically selected, which enables a good or optimum view of the patient. Furthermore, images captured by a plurality of cameras can be automatically or manually selected and/or arranged by the user on the field of view of the output unit. The quality of the monitoring of the patient may advantageously be increased further as a result.

In a further embodiment of the inventive method the process data is selected from:
optical image data from the examination space,
an item of patient information,
a medical parameter of the patient and/or
a parameter of the imaging examination,
wherein processing the process data comprises ascertaining a priority of the process data and
wherein the information in respect of the imaging examination is provided as a function of the ascertained priority.

Ascertaining the priority can in particular comprise determining the importance of different process data with regard to a physiological condition of the patient and/or a relevance of the process data for the monitoring of the patient. The process data can be classified with regard to the priority, sorted and/or compared with a predetermined reference value. In an exemplary embodiment, processing of the process data is limited to process data, which overshoots the predetermined reference value and/or a predetermined rank in a priority list.

Ascertaining the information in respect of the imaging examination can advantageously be restricted to relevant process data by ascertaining the priority of the process data. Computing effort, which is associated with the inventive method, can thus be reduced. Furthermore, overlaying the view of the patient with items of information in respect of the imaging examination may advantageously be avoided.

In accordance with a further embodiment of the inventive method, processing the process data comprises correlating optical image data with further process data. Correlating optical image data with further process data can in particular comprise correlating vital data of the patient with a position of the patient in the examination space. The vital data can be arranged on the patient in the field of view of the output unit. It is likewise conceivable that correlating optical image data with further process data comprises ascertaining a current position of the patient using the optical image data and correlating the current position of the patient with a desired position of the patient. The desired position of the patient can be ascertained for example as a function of a parameter of the imaging examination. In particular a deviation between the current position of the patient and the desired position of the patient can be ascertained. Correlating optical image data with further process data can also comprise correlating an imaging-relevant component with any information in respect of the imaging examination, which relates to the imaging-relevant component at a given instant.

Furthermore, providing the information in respect of the imaging examination comprises overlaying a predetermined field of view of the output unit with a graphical representation of the further process data as a function of the correlated process data. For example, the deviation can be provided in the form of a marking and/or a graphical representation and be overlaid on the user's field of vision of the patient. It is likewise conceivable, however, that items of information in respect of the imaging examination based on vital data of the patient in the form of a graphical representation are overlaid on the user's field of vision of the patient. Providing the information in respect of the imaging examination can in particular comprise an application of expanded reality and/or mixed reality. The perception of the user (in particular the monitoring of the patient) can be expanded or enriched in a computer-assisted manner here by items of information in respect of the imaging examination.

The user's perception with regard to monitoring of the patient can advantageously be extended to relevant aspects of the process data by overlaying captured optical image data and/or the predetermined field of view of the output unit with a graphical representation of further process data. Monitoring of the patient can consequently also consider items of information, which are not incorporated by an area of perception of the user.

In a further embodiment of the inventive method, capturing process data comprises capturing a parameter of the imaging examination, wherein processing the process data comprises ascertaining an item of time information in respect of a procedure of the imaging examination as a function of the parameter of the imaging examination. The parameter of the imaging examination can in particular comprise a duration of an imaging sequence, a segment of an imaging sequence, a succession of imaging sequences, but also an administered quantity of a contrast medium, a duration of an effect of the contrast medium, an available quantity of the contrast medium, a time difference from a subsequent imaging examination, overrunning of a booked duration for the imaging examination or the like. The item of time information ascertained as a function of the parameter of the imaging examination may be characterized by an item of information about a remaining period, which is available for implementation of a segment or procedure of the imaging examination.

Providing the information in respect of the imaging examination comprises providing an ascertained item of time information as a function of the procedure of the imaging examination. The ascertained item of time information may be overlaid by means of the output unit on the field of vision of the user during visual monitoring of the patient.

The user is able to consider a duration of a procedure of the imaging examination during monitoring of the patient by providing the ascertained item of time information. This can advantageously assist the user with a decision to continue, to interrupt or to repeat the procedure of the imaging examination in the case of peculiar behavior of the patient.

The inventive computer program product can be loaded directly into a memory of a computing unit of an inventive monitoring system in accordance with an above-described embodiment, with program code means in order to carry out an inventive method according to an above-described embodiment when the computer program product is executed in the computing unit of the monitoring system.

The computing unit of the monitoring system can be integrated in a controller and/or computing unit of the imaging apparatus or be in the form of a stand-alone computing unit of the monitoring system. The inventive method can be carried out quickly, in an identically repeatable manner and robustly by way of the inventive computer program product. The computer program product is configured such that it can carry out the inventive method steps by means of the computing unit. The computing unit in each case has to have the requirements, such as an appropriate main memory, an appropriate graphics card, an appropriate image processing unit or an appropriate logic unit, so the respective method steps can be efficiently carried out. The computer program product is saved for example on a computer-readable medium or stored on a network, a server or a Cloud from where it can be loaded into the processor of a local computing unit.

Furthermore, control information of the computer program product can be saved on an electronically readable data carrier. The control information of the electronically readable data carrier can be configured in such a way that it carries out an inventive method when the data carrier is used in the computing unit of the monitoring system. Examples of electronically readable data carriers are a DVD, a magnetic tape, a USB stick or any other data storage unit on which electronically readable control information, in particular software, is saved. When this control information is read from the data carrier and transferred to the computing unit, all inventive embodiments of the described inventive method can be carried out.

The inventive monitoring system and the inventive method relate in particular to a local implementation or a local construction in a control room of an imaging apparatus. In contrast to remote access or a remote application, the user is consequently able to independently intervene and/or initiate appropriate measures in case of an emergency, which is established for example by means of visual monitoring of the patient.

Figure 1:
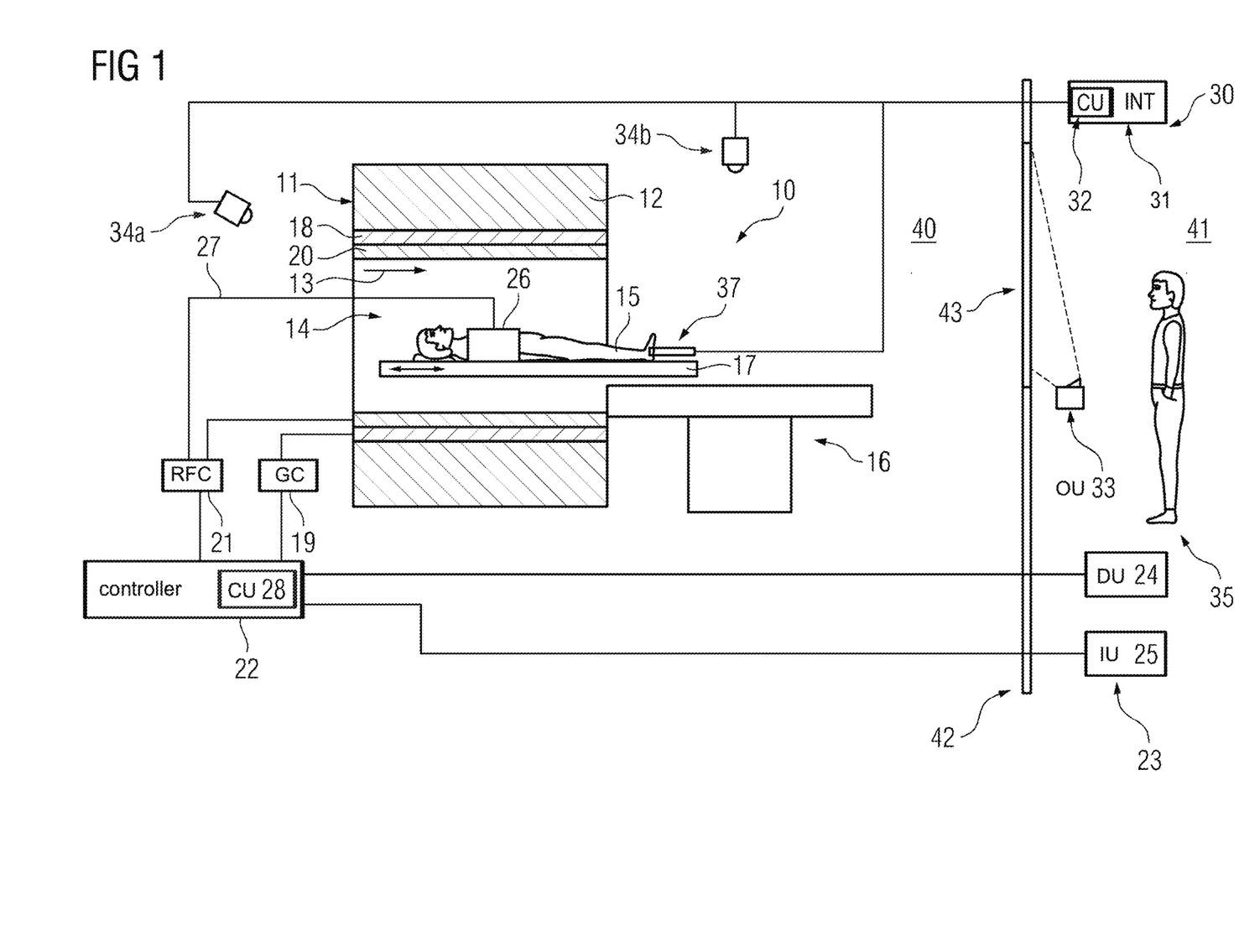
FIG. 1 is an imaging apparatus with a monitoring system according to an exemplary embodiment of the present disclosure.

FIG. 1 represents an exemplary embodiment of the inventive imaging apparatus 10. In the present case, the imaging apparatus 10 may be configured as a magnetic resonance apparatus 10. It is likewise conceivable, however, that the imaging apparatus 10 is configured as a computed tomography unit, an X-ray apparatus, a mammography apparatus, a positron emission tomography unit, a single photon emission computed tomography unit or the like. The magnetic resonance apparatus 10 comprises a magnetic unit 11, which has for example a permanent magnet, an electromagnet or a superconducting main magnet 12 for generating a strong and, in particular, homogeneous main magnetic field 13. In addition, the magnetic resonance apparatus 10 comprises a patient-receiving region 14 for receiving a patient 15. In the present exemplary embodiment, the patient-receiving region 14 may be cylindrical and surrounded in a circumferential direction by the magnetic unit 11. In principle, designs of the patient-receiving region 14 differing from this example are also conceivable, however.

The patient 15 can be positioned in the patient-receiving region 14 by means of a patient positioning apparatus 16 of the magnetic resonance apparatus 10. For this purpose, the patient positioning apparatus 16 has a patient couch 17 configured to move inside the patient-receiving region 14. The magnetic unit 11 also has a gradient coil 18 for generating magnetic gradient fields, which is used for spatial encoding during imaging. The gradient coil 18 may be actuated by means of a gradient controller 19 of the magnetic resonance apparatus 10. The magnetic unit 11 can also comprise a radio-frequency (RF) antenna, which in the present exemplary embodiment may be designed as a body coil 20 permanently integrated in the magnetic resonance apparatus 10. The body coil 20 may be configured to excite nuclear spins, which are located in the main magnetic field 13 generated by the main magnet 12. The body coil 20 may be actuated by a radio frequency (RF) controller 21 of the magnetic resonance apparatus 10 and irradiates radio-frequency excitation pulses into an image acquisition region, which is formed substantially by a patient-receiving region 14 of the magnetic resonance apparatus 10. The body coil 20 can also be configured to receive magnetic resonance signals. In an exemplary embodiment, the magnetic resonance apparatus 10 (which may include one or more components of the magnetic resonance apparatus 10) includes processing circuitry that is configured to perform one or more functions and/or operations of the magnetic resonance apparatus 10 (and/or its component(s)).

The magnetic resonance apparatus 10 has a controller 22 configured to control the main magnet 12, the gradient controller 19, and/or the RF controller 21. The controller 22 may be configured to control an implementation of a sequence, such as an imaging GRE (gradient echo) sequence, a TSE (turbo spin echo) sequence or a UTE (ultra-short echo time) sequence. In an exemplary embodiment, the controller 22 includes processing circuitry that is configured to perform one or more functions and/or operations of the controller 22.

In an exemplary embodiment, the controller 22 may include a computing unit (computer or computing device) 28 for evaluating magnetic resonance data, which is captured during a magnetic resonance examination. The computing unit 28 of the magnetic resonance apparatus 10 can be configured to use reconstruction methods to reconstruct diagnostic images of the patient 15 on the basis of the magnetic resonance data. In an exemplary embodiment, one or more components of the controller 22, such as the computing unit 28, includes processing circuitry that is configured to perform one or more respective functions and/or operations of the component(s).

Furthermore, the magnetic resonance apparatus 10 comprises a user interface 23, which has a signal link to the controller 22. Control information, such as imaging parameters, but also reconstructed magnetic resonance images, can be displayed for a user on a display unit 24, for example on at least one monitor, of the user interface 23. Furthermore, the user interface 23 has an input unit (input interface) 25, by means of which parameters of a magnetic resonance examination can be input by the user. The input unit 25 may include, for example, a keyboard, mouse, touchscreen, microphone, or the like.

FIG. 1 also shows a monitoring system 30 with an output unit (output interface) 33 which may be configured to overlay an item of information in respect of an imaging examination on a field of vision of a user 35 during visual monitoring of the patient 15. In the present case, the output unit 33 is configured as a projector 33, which may be configured to project items of information in respect of the imaging examination 36 in the field of vision of the user 35 onto a surface of the monitoring window 43. In the example shown the projector 33 together with the user 35 is positioned in a control room 41, while the patient 15 and the magnetic resonance apparatus 10 are positioned in the examination space 40.

It is conceivable that the user interface 23 is coupled to the monitoring system 30, enabling control of the output unit 33 by means of the input unit 25. Furthermore, the interface 31 of the monitoring system 30 can have a signal link to the controller 22 and/or the computing unit 28 of the magnetic resonance apparatus in order to receive process data, such as a parameter of the imaging examination. In an exemplary embodiment, the interface 31 includes processing circuitry that is configured to perform one or more functions of the interface 31. In an exemplary embodiment, one or more components of the interface 31, such as the computing unit 32, includes processing circuitry that is configured to perform one or more respective functions and/or operations of the component(s).

Just like the display unit 24, the output unit 33 can also be configured to enable control information to be displayed to the user 35 and/or an input of a parameter of the magnetic resonance examination. In the example shown in FIG. 1 the monitoring system 30 also has two cameras 34a and 34b, which capture optical image data of the patient 15 and transfer it to the interface 31 of the monitoring system 30. The computing unit 32 may be configured to actuate the projector 33 to project the optical image data of the cameras 34a and 34b onto the monitoring window 43 as images and/or as a video stream in a field of vision of the user 35 during visual monitoring of the patient 15. Of course, cameras 34 can also be arranged in a configuration different from the representation shown. For example, at least one camera 34 can be arranged in such a way that it mimics or imitates a view of the user 35 of the patient 15 through a monitoring window 43. It is likewise conceivable that at least one camera 34 is arranged outside of the examination space 40, for example in a patient-waiting area.

Furthermore, the inventive monitoring system 30 comprises a sensor 37, which is positioned on the patient 15 and may be configured to capture vital data of the patient 15.

The magnetic resonance apparatus 10 can also have a local receiving antenna 26, which is positioned on a body region of the patient 15 and detects magnetic resonance signals of the body region of the patient 15 and transfers them to the computing unit 28 of the controller 22. The local receiving antenna 26 may include an electric connecting cable 27, which provides a signal link to the RF controller 21 and the controller 22. Just like the body coil 20, the local receiving antenna 26 can also be designed for excitation of nuclear spins and for receiving magnetic resonance signals. The local receiving antenna 26 can be actuated by the RF controller 21 for this purpose. In the present example, the local receiving antenna 26 may be configured as a lay-on coil, which at least partially surrounds the chest of the patient 15.

The represented magnetic resonance apparatus 10 can of course comprise further components, which magnetic resonance apparatuses conventionally have. The magnetic resonance apparatus 10 can in particular be designed to carry out a magnetic resonance examination of a body region of the patient 15 in order to capture diagnostic image data of the body region of the patient 15.

Figure 2:
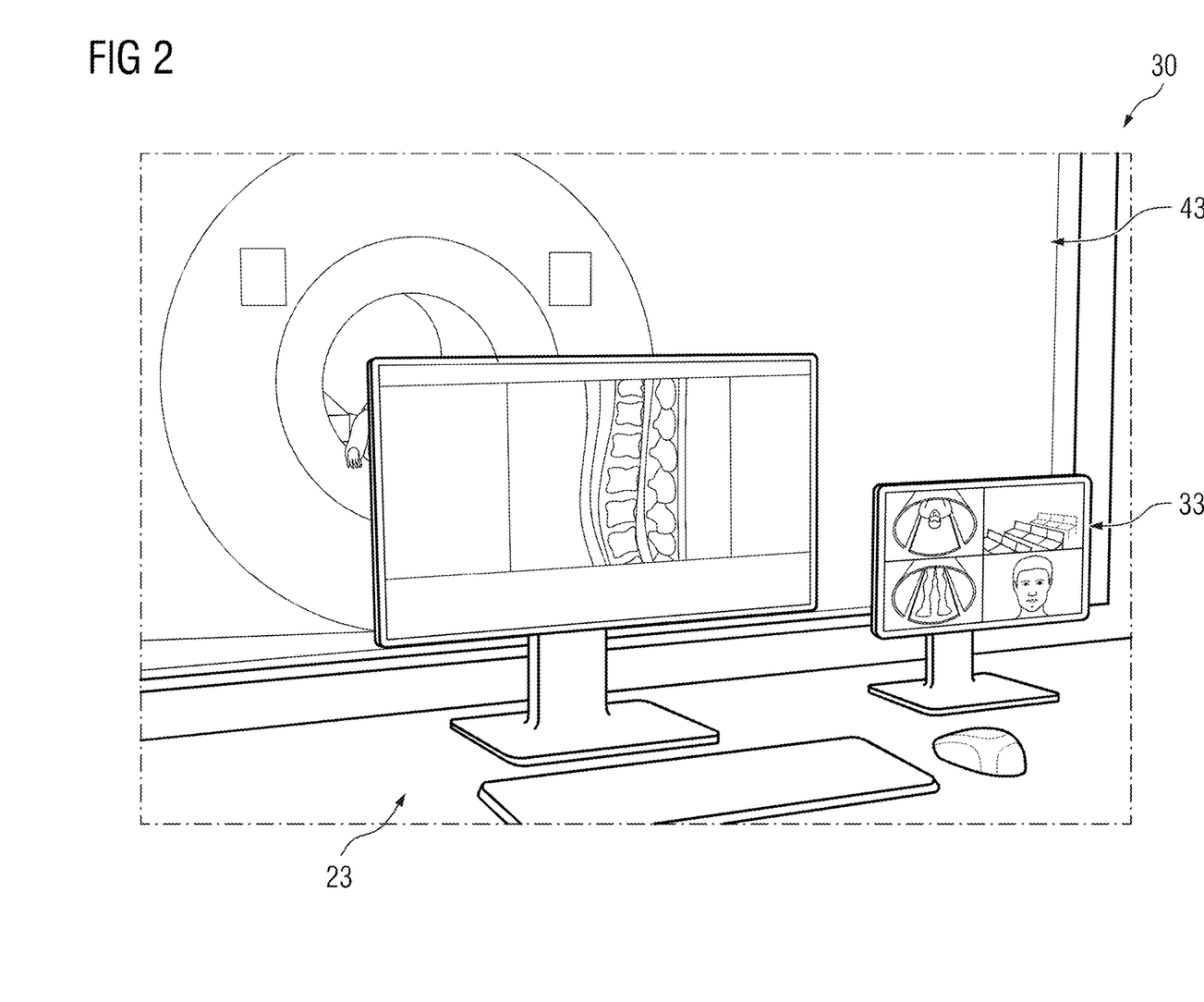
FIG. 2 is a monitoring system according to an exemplary embodiment of the present disclosure.

FIG. 2 shows an embodiment of the monitoring system 30 in which the output unit 33 is configured as a screen. The screen 33 can replace the monitoring window 43 or be installed in the control room 41 as an addition to the monitoring window 43. In the present case, the screen 33 is subdivided into four regions, which provide different items of information in respect of the imaging examination, in particular video signals from different cameras. In the present case, the screen 33 is positioned in front of the monitoring window 43 in such a way that the items of information in respect of the imaging examination provided by the screen 33 are overlaid on a view of the user 35 of the patient 15 (not represented) through the monitoring window 43. It is also conceivable that images of the patient 15 are overlaid on the screen 33 by way of information in respect of the imaging examination 36. Image data or video signals of one of more camera(s) 34 can be implemented on the monitoring system 30 for example in accordance with an ONVIF standard or a comparable standard.

Figure 3:
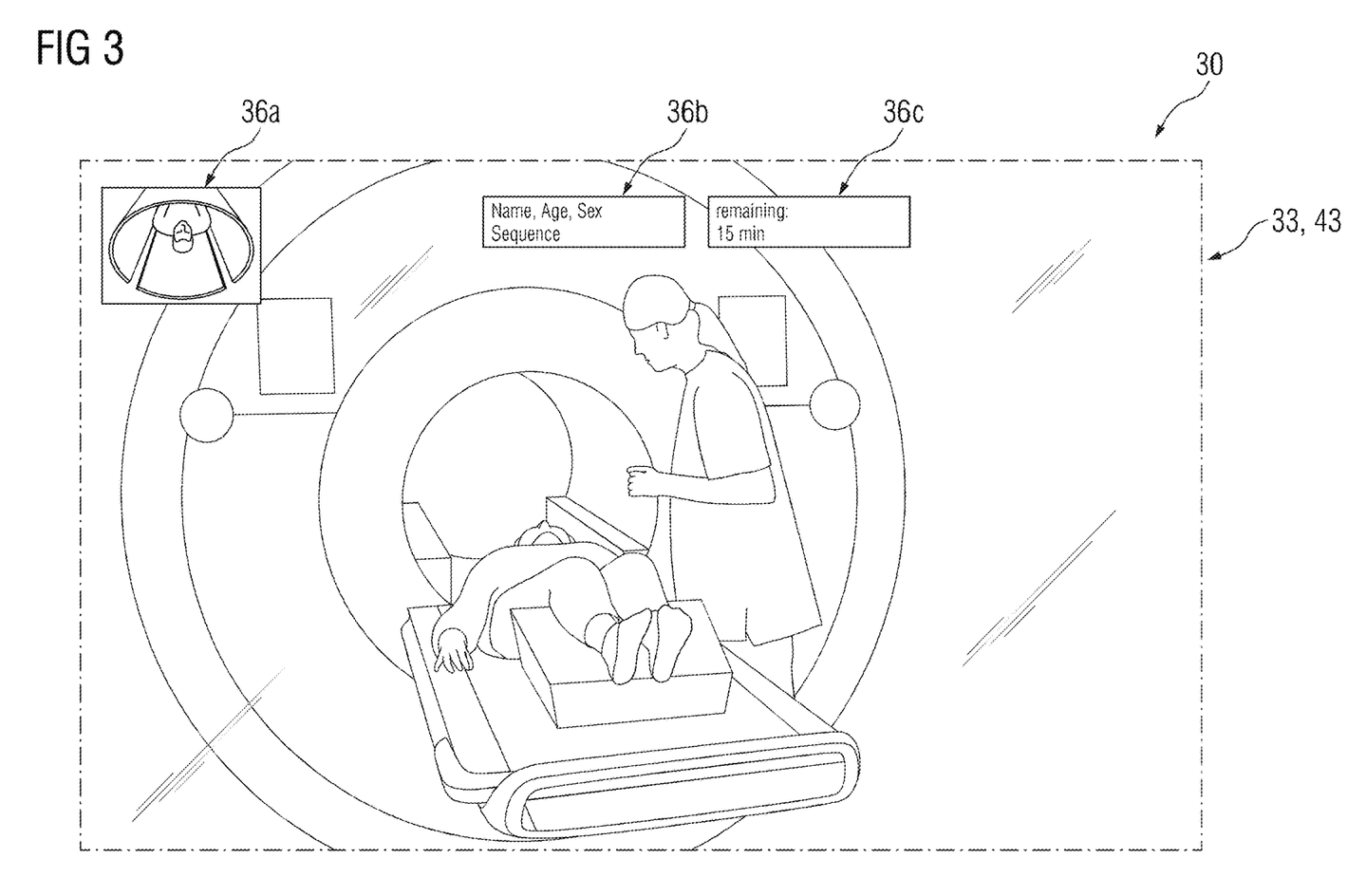
FIG. 3 is a monitoring system according to an exemplary embodiment of the present disclosure.

FIG. 3 shows an embodiment of the monitoring system 30 in which the output unit 33 may be configured as a transparent screen or a projector. In the represented example, items of information in respect of the imaging examination 36a, 36b and 36c (36a-c) are overlaid on a field of vision of the user 35 during visual monitoring of the patient 15. The user 35 is thus able to directly access selected items of information in respect of the imaging examination 36a-c in his field of vision and take them into account during monitoring of the patient 15 and/or the implementation of the imaging examination. The items of information in respect of the imaging examination 36a-c are based for example on particularly relevant or prioritized process data, which is ascertained by the computing unit 32. In the case of a transparent screen 33, the monitoring window 43 can simultaneously comprise the output unit 33. In the case of a projector 33, the monitoring window 43 can be separate from the output unit 33. The transparent screen 33 can also have a touchscreen functionality to enable an adjustment of a parameter of the imaging apparatus 10 without interrupting the visual monitoring of the patient 15.

In the example shown the information in respect of the imaging examination 36a comprises a video stream of the patient 15, which is based on optical image data of a camera 34. The items of information in respect of the imaging examination 36b and 36c, by contrast, comprise patient information, such as a name of the patient 15, and items of information about a type (for example "Brain Routine") and a progression (for example "Remaining 15 min") of the imaging examination.

Figure 4:
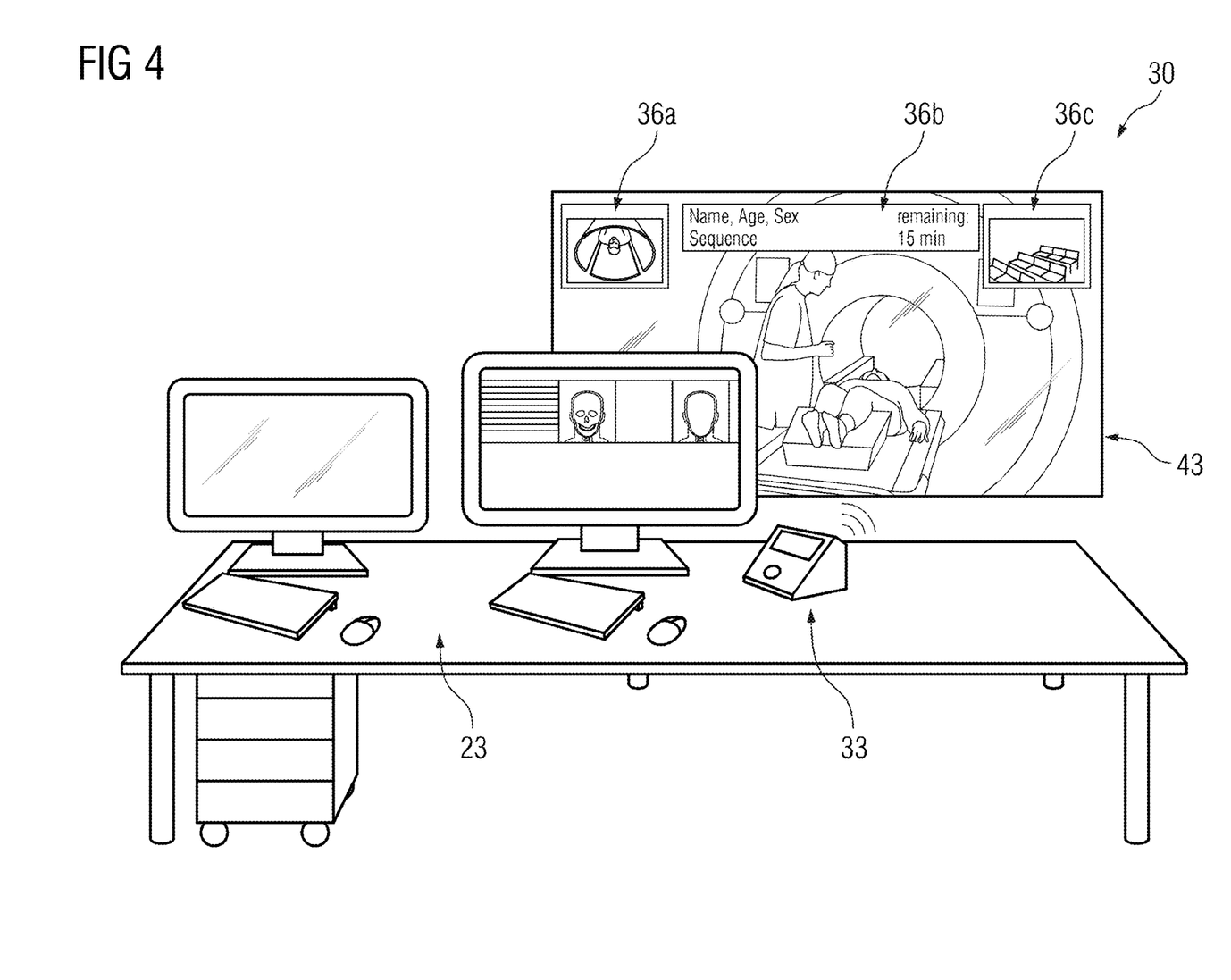
FIG. 4 is a monitoring system according to an exemplary embodiment of the present disclosure.

FIG. 4 shows a further embodiment of the inventive monitoring system 30 in which the output unit 33 is configured as a projector or a transparent screen. The items of information in respect of the imaging examination 36a-c can also comprise a n item of patient information of a subsequent patient here, but also optical image data from a patient waiting area. The computing unit 32 can have a signal link to a camera 34 in the patient waiting area for this purpose. The user 35 can thus be provided with a view into the patient waiting area. The user 35 is thus able to assess a condition of the current patient 15 and further patients in the waiting area while the current patient 15 is being examined in the imaging apparatus 10.

It is also conceivable that a functionality of the user interface 23 is integrated in the monitoring system 30. This can mean that the user 35 can view and/or process diagnostic images of the body region of the patient 15 by means of the output unit 33. The monitoring system 30 can also have an input unit, which enables modifying of a parameter of the imaging examination, but also of an item of patient information. In an exemplary embodiment, the user interface 23 (which may include display unit 24 and/or input unit 25), interface 31, output unit 33, and/or camera(s) 34 includes processing circuitry that is configured to perform one or more respective functions and/or operations of the component(s).

Figure 5:
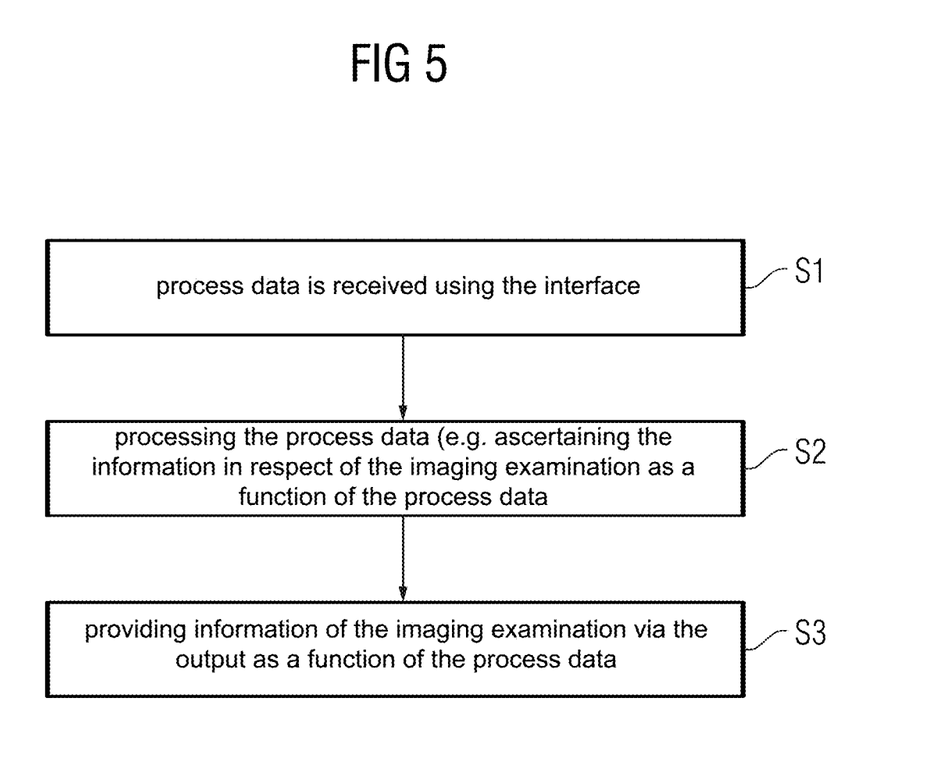
FIG. 5 is a flowchart of a method according to an exemplary embodiment of the present disclosure.

FIG. 5 shows one possible flowchart of an inventive method for providing an item of information in respect of an imaging examination 36 of a patient 15, with a monitoring system 30 with an interface 31, a computing unit 32 and an output unit 33.

In a step S1, process data is received by means of the interface 31. The process data may include optical image data from a camera 34. It is likewise conceivable, however, that the interface 31 has a signal link to the controller 22 and/or computing unit 28 of the imaging apparatus 10 in order to receive parameters of the imaging examination. In a further embodiment the interface 31 has a signal link to at least one sensor 37 in the examination space. The at least one sensor 37 can be designed in particular to acquire physiological or vital data of the patient 15. The process data can also comprise an item of patient information or a medical parameter of the patient.

In a step S2, the process data is processed by means of the computing unit 32. Processing of the process data can in particular comprise ascertaining the information in respect of the imaging examination 36 as a function of the process data. In one example, processing the process data can also comprise ascertaining a primary camera 34 of a plurality of cameras 34 as a function of a position of the patient 15 relative to the imaging apparatus 10.

In a further step S3, the information in respect of the imaging examination 36 is provided as a function of the process data by means of the output unit 33.

In a further example, processing the process data comprises ascertaining a priority of the process data. The items of information in respect of the imaging examination 36 provided to the user 35 are selected as a function of the ascertained priority of the process data and overlaid on the field of vision of the user 35 of the patient 15.

Processing the process data can also comprise correlating optical image data with further process data. For example, a current position of the patient 15 can be compared with a desired position of the patient 15 and/or a deviation between the current position of the patient 15 and the desired position of the patient 15 can be ascertained here. The ascertained deviation can be overlaid as information in respect of the imaging examination on the field of vision of the user 35 by means of the output unit 33 during visual monitoring of the patient 15.

Processing the process data can also comprise ascertaining an item of time information in respect of a procedure of the imaging examination as a function of the parameter of the imaging examination. As shown in FIG. 3 and FIG. 4, the item of time information can be provided in the field of vision of the user 35 by means of the output unit 33.

Of course, the embodiments of the inventive method and of the inventive imaging apparatus described here should be understood as being exemplary. Individual embodiments can therefore be expanded by features of other embodiments. In particular, the order of the method steps of the inventive method should be understood as being exemplary. The individual steps can also be carried out in a different order or partially or completely overlap timewise.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A monitoring system for monitoring a patient in an examination space of an imaging apparatus, comprising:
   an interface configured to receive process data in respect of an imaging examination, the process data including optical image data of a plurality of cameras;
   a computing device configured to:
     process the process data received from the interface, the processing of the process data including determining a position of the patient relative to the imaging apparatus and determining, based on the position of the patient relative to the imaging apparatus, a primary camera of the plurality of cameras, and
     control an output device to provide information corresponding to the imaging examination based on the process data; and
   the output device that is configured to generate a visual representation of the information based on the process data to enable visual monitoring of the patient and of the information corresponding to the imaging examination, the generation of the visual representation of the information including outputting images of the primary camera.

2. The monitoring system as claimed in claim 1, wherein the output device comprises a projector configured to project the information corresponding to the imaging examination onto a monitoring window of the examination space, the monitoring window being configured to enable a user of the imaging apparatus to view the patient in the examination space, and wherein the computing device is configured to control the output device to overlay the information, using the projector, on a field of vision of the user through the monitoring window.

3. The monitoring system as claimed in claim 2, wherein the output device further comprises a transparent screen configured to enable the user to view the examination space through the transparent screen, and wherein the computing device is configured to control the output device to overlay the information, using the transparent screen, on the field of vision of the user through the transparent screen.

4. The monitoring system as claimed in claim 1, wherein the output device includes a transparent screen configured to enable a user of the imaging apparatus to view the examination space through the transparent screen, and wherein the computing device is configured to control the output device to overlay the information, using the transparent screen, on a field of vision of the user through the transparent screen.

5. The monitoring system as claimed in claim 1, further comprising: a camera positioned in the examination space and configured to capture optical image data of the patient in the examination space and transfer the captured optical image data to the interface, wherein the computing device is configured to create one or more images of the patient based on the captured optical image data.

6. The monitoring system as claimed in claim 5, wherein the output device comprises a screen and wherein the computing device is configured to provide the one or more images of the patient in the examination space using the screen.

7. The monitoring system as claimed in claim 1, further comprising at least one sensor positioned in the examination space of the imaging apparatus and configured to capture the process data from the examination space, wherein the interface is configured to receive the process data from the at least one sensor and transfer the received process data to the computing device, the information being based on the process data of the at least one sensor.

8. The monitoring system as claimed in claim 7, wherein the at least one sensor is configured to capture, as the process data:
   a medical parameter of the patient,
   a parameter of an imaging-relevant component, and/or
   a measured value of a medical device.

9. The monitoring system as claimed in claim 1, wherein the interface comprises a signal link to the imaging apparatus and is configured to receive the process data from the imaging apparatus and transfer the received process data to the computing device, wherein the process data relates to a parameter of the imaging examination and/or an item of patient information.

10. The monitoring system as claimed in claim 1, wherein the computing device is configured to:
    provide a plurality of items of information corresponding to the imaging examination, using the output device, and
    adjust a type, an arrangement and/or an instant of the provided plurality of items of information based on the process data.

11. The monitoring system as claimed in claim 1, wherein the imaging apparatus is a medical device configured to capture image data of a body region of the patient.

12. A method for providing information, using a monitoring system, of an imaging examination of a patient using an imaging apparatus, the method comprising:
    receiving process data using an interface, including receiving optical image data of a plurality of cameras;
    processing the process data using a computing device, including determining a position of the patient relative to the imaging apparatus and determining, based on the position of the patient relative to the imaging apparatus, a primary camera of the plurality of cameras; and
    controlling, using the computing device, an output device to:
      generate a visual representation of the information of the imaging examination based on the process data; and
      provide the visual representation of the information as an output of the monitoring system, including outputting images of the primary camera using the output device.

13. The method as claimed in claim 12, wherein:
    the process data comprises:
      optical image data from the examination space,
      an item of patient information,
      a medical parameter of the patient, and/or
      a parameter of the imaging examination;

processing the process data comprises determining a priority of the process data; and providing the visual representation of the information based on the determined priority.

14. The method as claimed in claim 12, wherein:

processing the process data comprises correlating optical image data with further process data; and providing the visual representation of the information comprises overlaying a predetermined field of view of the output device with a graphical representation of the further process data based on the correlated process data.

15. The method as claimed in claim 12, wherein:

receiving process data comprises acquiring a parameter of the imaging examination;

processing the process data comprises determining an item of time information of a procedure of the imaging examination based on the parameter of the imaging examination; and providing the visual representation of the information comprises providing the ascertained item of time information based on the procedure of the imaging examination.

16. A computer program product, embodied on a non-transitory computer-readable medium, which includes program code and can be loaded directly into a memory of a computing device of a monitoring system, when executed by the computing device, causes the computing device to perform the method of claim 12.

17. A non-transitory computer-readable storage medium with an executable program stored thereon, that when executed, instructs a processor to perform the method of claim 12.

18. The method as claimed in claim 12, wherein the imaging apparatus is a medical device configured to capture image data of a body region of the patient.

19. A monitoring system for monitoring a patient in an examination space of an imaging apparatus, comprising:

an interface configured to receive process data in respect of an imaging examination;

a computing device configured to: process the process data received from the interface, and control an output device to provide information corresponding to the imaging examination based on the process data; and the output device that is configured to generate a visual representation of the information based on the process data to enable visual monitoring of the patient and of the information corresponding to the imaging examination, wherein the output device comprises a projector configured to project the information corresponding to the imaging examination onto a monitoring window of the examination space, the monitoring window being configured to enable a user of the imaging apparatus to view the patient in the examination space, the computing device being configured to control the output device to overlay the information, using the projector, on a field of vision of the user through the monitoring window.

20. The monitoring system as claimed in claim 19, wherein the projector is positioned inside a control room outside of the examination space and separated from examination space by the monitoring window.

* * * * *